United States Patent [19]

Campbell

[11] Patent Number: 4,799,923

[45] Date of Patent: Jan. 24, 1989

[54] MEDICAL TUBE SECURING DEVICE

[76] Inventor: Myrna Campbell, 304 Acorn Dr., Lafayette, La. 70507

[21] Appl. No.: 906,889

[22] Filed: Sep. 15, 1986

[51] Int. Cl.⁴ ............................................. A61M 25/02
[52] U.S. Cl. ............................ 604/179; 128/DIG. 26
[58] Field of Search ............................... 604/174–180, 604/327, 345; 128/DIG. 26

[56] References Cited

U.S. PATENT DOCUMENTS

| | | | |
|---|---|---|---|
| 2,476,513 | 7/1949 | Scott | 604/345 |
| 2,612,895 | 10/1952 | Magee | 604/327 |
| 2,788,785 | 4/1957 | Present | 604/345 |
| 3,752,162 | 8/1973 | Newash | 604/93 |
| 4,517,971 | 5/1985 | Sorbonne | 604/174 X |
| 4,569,348 | 2/1986 | Hasslinger | 604/179 |
| 4,571,245 | 2/1986 | Hubbard et al. | 604/179 |
| 4,578,062 | 3/1986 | Schneider | 604/174 |
| 4,582,508 | 4/1986 | Pavelka | 604/179 |
| 4,596,560 | 6/1986 | Simpson | 604/174 |

Primary Examiner—Dalton L. Truluck
Attorney, Agent, or Firm—Keaty & Keaty

[57] ABSTRACT

A medical tube securing device, for securing tubes such as gastrostomy tubes which project from a person's body, comprises an openable pouch having a hole in the back portion thereof. A tube is pulled through the hole in the pouch, the pouch is secured to the body of the user, and the pouch is closed, thereby enclosing therewithin the free portion of the tube. In this manner, the portion of the tube projecting from the user's body is neither suceptible to being pulled by the user's hands, nor likely to be engaged by objects around the user; hence, the incidence of accidental, premature removal of the tube is greatly reduced.

In an alternate embodiment, fasteners are also provided to reduce the possibility of the tube sliding into the user's body.

4 Claims, 3 Drawing Sheets

MEDICAL TUBE SECURING DEVICE

BACKGROUND OF THE INVENTION

1. Field of the Invention

The present invention relates to a securing device for medical tubes projecting from a person's body, and more particulary to a pouch-like securing device for medical tubes.

2. General Background of the Invention

Due to various disorders, certain bodily functions must be aided by means of medical tubes inserted into the body. (As used herein, the term "medical tubes" refers to tubes which are used to bypass portions of the human body to aid certain bodily functions; examples of such tubes are catheters and gastrostomy tubes.) For example, in the case of chronic reflux of food from the esophagus into the trachea, some persons must be fed through a gastrostomy tube inserted through a surgically-created hole in the abdominal wall (a gastric fistula) into the stomach. The purpose of the tube is to provide a means of feeding a person who could not otherwise be fed. Persons who might have extreme difficulty with feeding include neurologically impaired persons, those who have a congenital deformity of the esophagus, and those who have had some accidental injury to the esophagus, resulting in interruption of the lumen. Additionally, the gastrostomy tube might be useful for persons who have had major surgery to the esophagus or for very debilitated individuals. The gastrostomy tube usually comprises a flexible tube having a pair of exit ports and a balloon at a first end thereof, and primary and secondary entry ports at the other end. The primary entry port is connected by a relatively large diameter passage to the exit ports, and serves to allow food to enter the stomach. The secondary entry port is connected by a relatively small diameter passage to the balloon, and serves to allow water to fill the balloon, which helps to retain the gastrostomy tube in place. An example of the gastrostomy tube described above is Bardex ® Silicone Elastomer Coated Foley Catheter manufactured by Bard Urological Division of C. R. Bard, Inc., Murray Hill, N.J.

In operation, the first end of the gastrostomy tube is inserted through a gastric fistula into the person's stomach. The balloon is filled by injecting sterile water through the secondary entry port. The gastostomy tube is then ready to be used to feed the person via the primary entry port; the tube may be used for a number of feedings. A portion of the tube, including the end having the entry ports, extends from the hole in the abdominal wall. This portion of the gastrostomy tube is typically troublesome for the person in whom the tube is placed, for it has a tendency to slip into the stomach or to be pulled out of the stomach. There are some methods for reducing the tendency of the tube to slide into the stomach, such as inserting the tube through a baby bottle nipple, before inserting the tube into the stomach, such that the base of the nipple is against the outside of the stomach and the nipple projects outwardly. Unfortunately, the base of the nipple often irritates the tissue on the outside of the stomach, so many people choose not to use it. While this option and others can help to prevent the tube from sliding into the stomach, there has heretofore been no satisfactory means for preventing the gastrostomy tube from being accidentally pulled out of the stomach. Regardless of how careful a person (whether he be a child or an adult) may be during the day, he may unintentionally pull out the gastrostomy tube while sleeping. Also, some persons who use gastrostomy tubes are mentally retarded, and frequently pull out their tubes simply because they do not understand why the tube is there. Still other persons using gastrostomy tubes are susceptible to involuntary muscular contractions, and may involuntarily pull out their tube during a spasm.

These tubes are not to be resterilized; once removed from the stomach, they may be be re-used. Since these tubes are relatively expensive, accidental premature removal is not only a source of discomfort for the user, it is also uneconomical. There are cases in which the tube must be replaced four times more frequently, due to premature accidental removal, than if it were to be replaced only when no longer operable, resulting in a four-fold increase in annual expenditures for gastrostomy tubes.

It can thus be seen that there exists a need for an effective means for reducing the chance of accidental premature removal of medical tubes such as gastrostomy tubes.

SUMMARY OF THE INVENTION

The present invention provides a means to reduce the incidence of accidental premature removal of medical tubes such as gastrostomy tubes.

The device of the present invention comprises an openable pouch means having an opening in the back thereof. The pouch means is securely attached by a securing means to a person's body, the medical tube is drawn through the opening, and the pouch means is closed, thereby enclosing, within the pouch means, the portion of the medical tube which protrudes from the user's body. With that portion of the tube enclosed within the pouch means, the medical tube is less susceptible to being accidentally pulled out of the body, reducing the discomfort and expense associated with premature removal of the medical tube.

In one embodiment of the present invention, means are provided within the pouch means to reduce the possibility of the medical tube accidentally sliding into the body, thereby avoiding, in many cases, the trouble and discomfort of locating and retrieving an end of the tube.

The pouch means and the means of attaching it to a person's body preferably comprise a soft, pliable, hypoallergenic fabric. All fastening and securing means preferably comprise mating hook-and-loop separable fasteners, such as those sold under the trademark Velcro. The use of such fabric and fasteners helps to insure that the device will be as comfortable as possible for the user. The securing means is adjustable in order to fit persons of varying size.

It is an object of the present invention to provide a securing device to reduce the possibility of accidental premature removal of a medical tube from a user's body.

Another object of the present invention is to provide a device which resists the tendency of the entire medical tube to slide into the body of a person using it.

A further object of the present invention is to provide a medical tube securing device which is comfortable and adjustable.

BRIEF DESCRIPTION OF THE DRAWINGS

For a better understanding of the objects and advantages of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
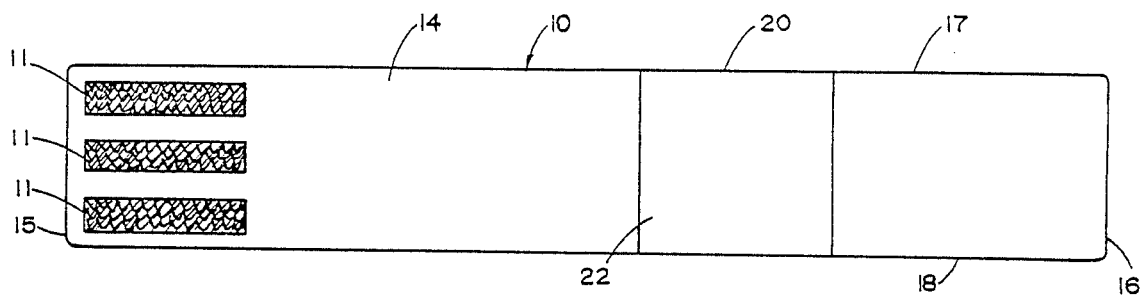
FIG. 1 is a front view of the preferred embodiment of the device of the present invention.
Figure 2:
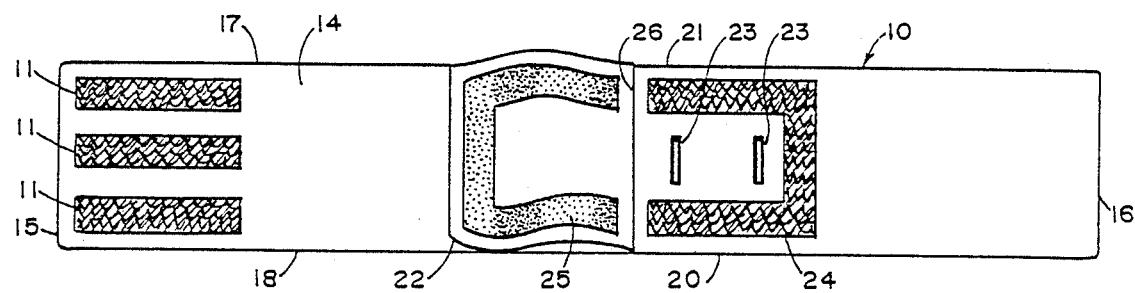
FIG. 2 is a front perspective view of the device shown in FIG. 1, with the pouch means in an open position.
Figure 3:
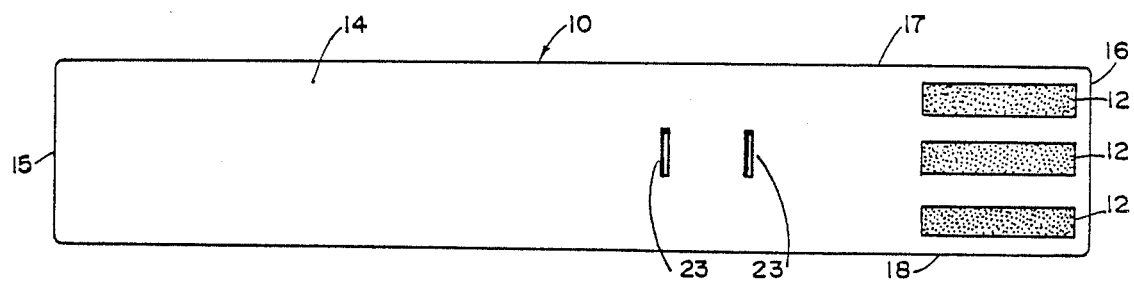
FIG. 3 is a rear view of the device shown in FIGS. 1 and 2.

Referring to FIGS. 1, 2 and 3, the medical securing device 10 of the preferred embodiment of the present invention comprises an elongate band 14 having first and second ends 15 and 16, respectively, and top and bottom edges 17 and 18, respectively. Fastening strips 12 are disposed adjacent second end 16 of elongate band 14. Elongate band 14 carries a pouch means comprising an openable pouch 20 having a back portion 21 formed on band 14 between top edge 17 and bottom edge 18, and a front or flap portion 22. Back portion 21 has a pair of openings 23 therein, each of which is large enough to pass the free end of a medical tube therethrough. Releasable fastening of the flap portion 22 to the back portion 21 is accomplished through the use of fastening strip 25 on front or flap portion 22 and fastening strip 24 on back portion 21. Fastening strip 24 preferably comprises a hook material having a plurality of small resilient hooks; fastening strip 25 preferably comprises a fibrous loop material (fastening means of this type are commercially available under the trademark Velcro). Fastening strips 25, 24 are stitched or otherwise secured to front and back portions 22, 21 of pouch 20, respectively. One edge 26 of flap portion 22 is sewn or otherwise secured to back portion 21 to prevent portions 21, 22 from being completely separated when pouch 20 is opened. Fastening strips 11 and 12 preferably comprise hook material and fibrous loop material, respectively. The material used to make medical tube securing device 10 preferably comprises a soft, pliable, hypo-allergenic fabric to minimize discomfort and irritation of the user.

Figure 5:
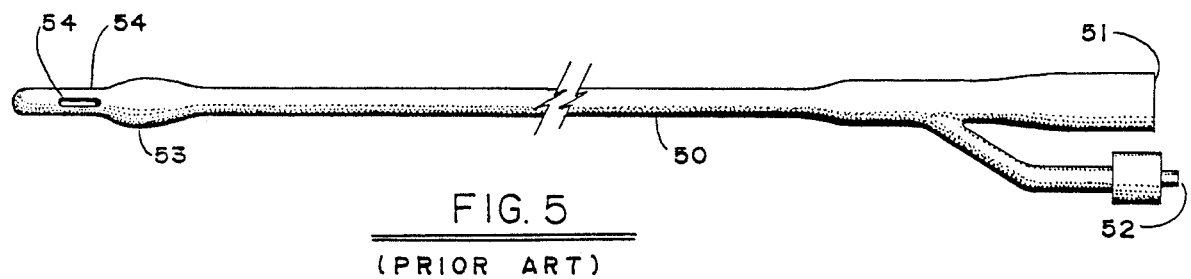
FIG. 5 is a perspective view of a commercially available gastrostomy tube which the device of the present invention is designed to secure.
Figures 6, 7:
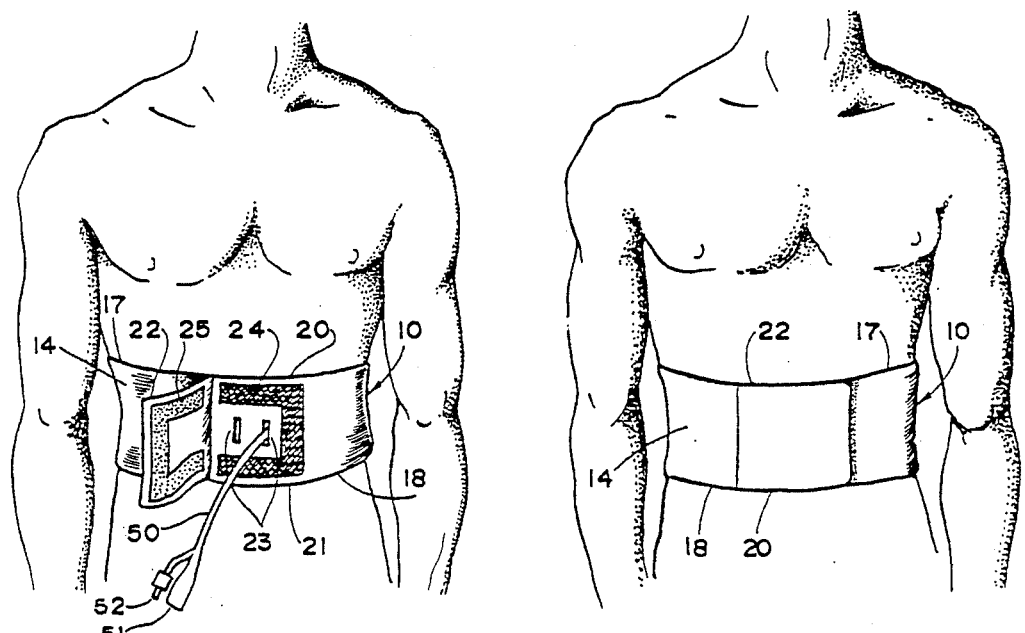
FIG. 6 is a perspective view of the device illustrated in FIGS. 1–3 being worn by a gastrostomy tube user, with the pouch means in an open position.
FIG. 7 is a view similar to that of FIG. 6, with the pouch means in a closed position.

The medical tube securing device of the present invention can be used to protect a medical tube such as the gastrostomy tube 50 illustrated in FIG. 5. In operation, gastrostomy tube 50 is inserted in the user through a gastric fistula (not shown). Water is injected into a secondary entry port 52, filling a balloon 53, which helps to place gastrostomy tube 50 correctly in the abdominal cavity of the user. Nutrients enter tube 50 via primary entry port 51, and exit tube 50 into the stomach of the user via exit ports 54. The end of tube 50 having entry ports 51 and 52 therein is pulled through the opening 23 which is on the same side of the body of the user as the gastric fistula (this allows pouch 20 to be approximately centered on the user's body). Medical tube securing device 10 is wrapped around the body of the user (FIG. 6) and secured thereto by placing first end 15 and second end 16 of elongate band 14 in juxtaposed relationship and engaging fastening strips 11 with fastening strips 12. The portion of tube 50 protruding from the stomach is then placed inside pouch 20, and pouch 20 is closed by engaging fastening strips 25 of flap portion 22 with fastening strip 24 of back portion 21. With the portion of tube 50 extending outwardly from the stomach now safely enclosed in pouch 20, the possibility of the outer end of tube 50 engaging with an object and causing tube 50 to be accidentally pulled from the user's stomach is reduced and, along with it, the expense and discomfort associated therewith. When the user is to be fed, pouch 20 is opened, and food is injected into primary entry port 51. When feeding is completed, pouch 20 is again closed to enclose the portion of gastrostomy tube 50 therewithin until the next feeding.

If the user has a baby bottle nipple (not shown) on the gastrostomy tube 50, the nipple may be pulled through the appropriate opening 23 in back portion 21 of pouch 20, such that the base of the nipple is on the opposite side of back portion 21 from the user's body. This reduces the area of contact of the nipple with the skin of the user, thereby helping to prevent irritation of the user's skin by the nipple.

Figure 4:
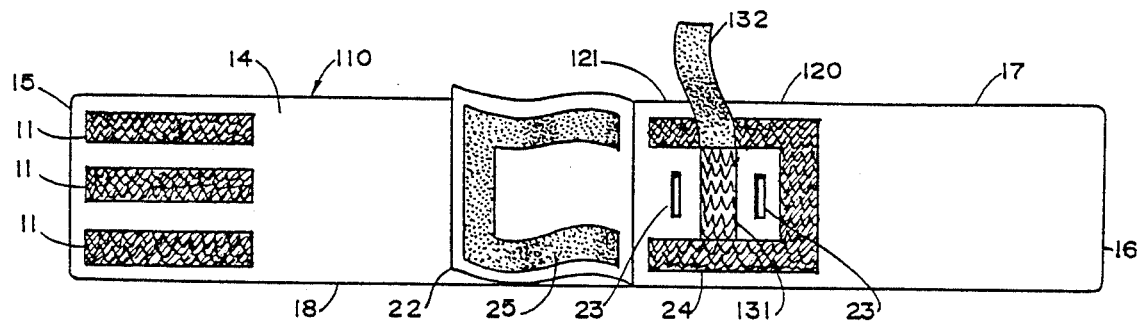
FIG. 4 is a front perspective view of a second embodiment of the device of the present invention.

A second embodiment of the device of the present invention comprises a medical tube securing device 110 (FIG. 4) having the elements described in conjunction with medical tube securing device 10, and further comprising a slide-resisting means to resist the tendency of the entire medical tube to slide into the body of the user. The slide-resisting means comprises a fastening strip 131, preferably comprising resilient hook material, stitched or otherwise secured to back portion 121 of pouch 120, and a fastening strip 132, preferably comprising fibrous loop material, attached at an end thereof to fastening strip 131.

Figure 8:
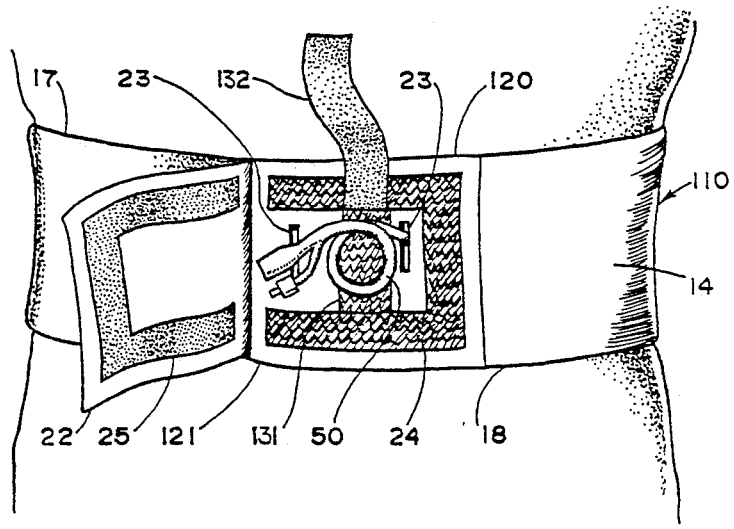
FIG. 8 is a perspective view of the device illustrated in FIG. 4 being worn by a user of a gastrostomy tube, the pouch means being shown in an open position.

Once the medical tube securing device 110 has been secured on the user's body, the portion of tube 50 projecting from the user's stomach is coiled and placed on fastening strip 131 (FIG. 8). Fastening strip 132 is then placed over fastening strip 131, and pressure is applied thereon at the center of, above, and below the coiled portion of tube 50, securing the coiled portion between fastening strips 131 and 132, thereby helping to prevent tube 50 from sliding into the user's stomach. Closing pouch 120 encloses the exterior portion of the tube 50 therein. It can thus be seen that medical tube securing device 110 not only reduces the possibility of tube 50 being pulled out of the user's stomach, but also reduces the chance that the exterior portion of tube 50 will slide into the stomach, thus eliminating the need for a baby bottle nipple on the gastrostomy tube or some other auxiliary means to resist the tendency of the exterior portion of the tube to slide into the stomach.

A third embodiment of the device of the present invention comprises a medical tube securing device 210

Figure 9:
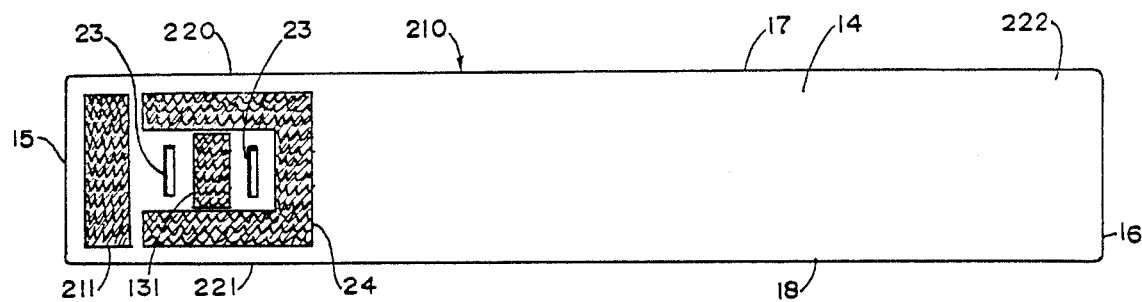
FIG. 9 is a front view of a third embodiment of the device of the present invention.
Figure 10:
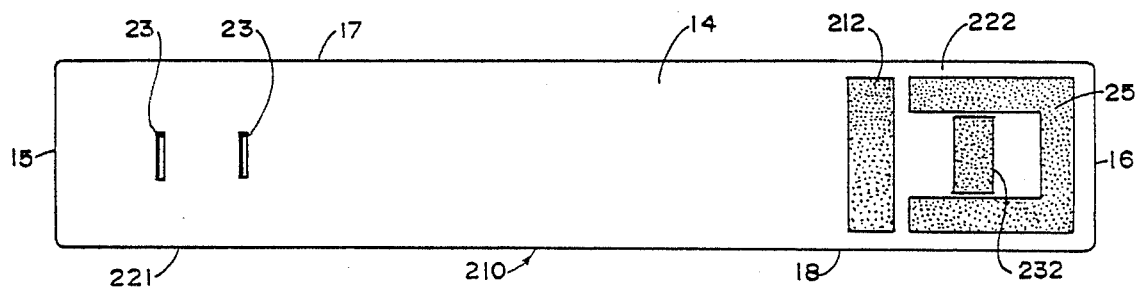
FIG. 10 is a rear view of the embodiment shown in FIG. 9.

(FIGS. 9 and 10) which is similar to the first two embodiments.

In operation, the exterior portion of tube 50 is drawn through the hole 23 which is on the same side of the body of the user as the gastric fistula. Medical tube securing device 210 is then wrapped around the body of the user, and is secured thereto by mating fastening strip 211 (which preferably comprises resilient hook material) with fastening strip 212 (which preferably comprises fibrous loop material). The exterior portion of gastrostomy tube 50 is then coiled on fastening strip 131 on back portion 221 of pouch 220; flap portion 222 of pouch 220 is pressed onto back portion 221, engaging fastening strip 131 with fastening strip 232 (which preferably comprises fibrous loop material), and fastening strip 24 with fastening strip 25, thereby securing the coiled portion of tube 50 between fastening strips 131 and 132, and enclosing it within pouch 220. As can be seen, this embodiment has as an advantage the positioning of all fastening and securing means on the front of the user's body; however, this is at the expense of adjustability of the device to the user's size.

While only three embodiments of the present invention have been shown and described, there are numerous modifications which could be made thereto without departing from the spirit or scope of the present invention. While a band of fabric has been found to work well to secure the pouch to a user's body, a plurality of strips of fabric could instead be used. One opening could be omitted, although that would reduce the ease of centering the pouch. Although the preferred fastening means are mating hook-and-look separable fasteners of the type sold under the trademark Velcro, other types of mating fasteners could be used, such as snap fasteners, buttons or zippers. Another modification could be to form the tube securing device as a single band of fabric, with a single opening near one end thereof. The side of the band facing the user's body could comprise fibrous loop material, with the other side comprising resilient hook material. With the outer portion of the tube pulled through the opening and coiled, the tube securing device would be wrapped around the user's body and the end of the tube securing device opposite the end near the opening would be placed over and beyond the tube, then pressed in place, thereby simultaneously enclosing the outer portion of the tube within the medical tube securing device and reducing the chance that the tube will slide into the user's body. Furthermore, while the operation of the tube securing device of the present invention has been described in conjunction with a gastrostomy tube, it can of course be used to protect other medical tubes, such as urinary tract catheters and drainage tubes. In view of the foregoing and other possible modifications to and uses of the embodiments of the present invention herein described, I pray that my rights to the present invention be limited only by the following claims.

I claim:

1. A securing device for a medical tube, a portion of which extends outwardly from a person's body, the device comprising:
   a pouch means for receiving the upwardly extending portion of the tube and retaining it in a substantially stable position in relation to the person's body;
   means for securing the pouch means in a substantially fixed relationship to the person's body, said means comprising an elongate flexible band having a front side, a back side, a first end and a second end, the ends being provided with mating fasteners adapted for securing the ends together in juxtaposed relationship and wherein the pouch means comprises a front portion and a back portion, the back portion being formed on the front side of the flexible band and the front portion being adapted for releasable fastening, in covering relationship, to the back portion, the back portion being provided with at least one opening for receiving the outwardly extending portion of the medical tube projecting therethrough; and
   wherein the pouch means is securely attached to the front side of the flexible band.

2. A method of securing a medical tube, a portion of which extends outwardly from a person's body, the method comprising the steps of:
   providing a substantially flat flexible pouch means securable on the outside of the person's body comprising a back portion and a front portion, the back portion being adapted for releasable fastening, in covering relationship, to the back portion;
   extending the outwardly extending portion of the medical tube through the opening in the back portion of the pouch means;
   covering the back portion of the pouch and the outwardly extending portion of the medical tube with the front portion of the pouch;
   providing securing means for securely positioning the pouch means in relation to the person's body; and
   securing the pouch means on the person's body, thereby securely positioning the outwardly extending portion of the medical tube in relation to the person's body.

3. The method of claim 2 further comprising the step of providing slide-resisting means for resisting sliding movement of the outwardly extending portion of the medical tube into the person's body, said slide-resisting means comprising a fastening band having mating fasteners disposed inside the pouch means.

4. A method of securing a medical tube, a portion of which extends outwardly from a person's body, the method of comprising the steps of:
   providing a pouch means comprising a back portion and a front portion, the back portion having at least one opening and the front portion being adapted for releasable fastening, in covering relationship, to the back portion;
   extending the outwardly extending portion of the medical tube through the opening in the back portion of the pouch means;
   covering the back portion of the pouch and the outwardly extending portion of the medical tube with the front portion of the pouch;
   providing securing means for securely positioning the pouch means in relation to the person's body, wherein the securing means comprises an elongate flexible band having a first end and a second end and having mating fasteners attached to the ends of the band for securing the ends together in juxtaposed relationship; and
   securing the pouch means on the person's body, thereby securely positioning the outwardly extending portion of the medical tube in relation to the person's body.

* * * * *